US006737531B1

(12) United States Patent
Dioumaev et al.

(10) Patent No.: US 6,737,531 B1
(45) Date of Patent: May 18, 2004

(54) CATALYSTS FOR HYDROGENATION AND HYDROSILYLATION, METHODS OF MAKING AND USING THE SAME

(75) Inventors: Vladimir K. Dioumaev, Coram, NY (US); R. Morris Bullock, Wading River, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 3 days.

(21) Appl. No.: 10/320,954

(22) Filed: Dec. 17, 2002

(51) Int. Cl.[7] ............................. C07F 11/00; C07F 7/04; B01J 31/00; C07C 29/14
(52) U.S. Cl. .................. 548/101; 502/152; 502/155; 556/59; 556/470; 556/482; 568/809; 568/814; 568/881
(58) Field of Search .................... 548/101; 556/59, 556/470, 482; 568/809, 814, 881; 502/152, 156

(56) References Cited

U.S. PATENT DOCUMENTS

| | | | |
|---|---|---|---|
| 3,931,242 A | 1/1976 | Dawans et al. | 260/846 |
| 5,182,246 A | 1/1993 | Fuchikami et al. | 502/161 |
| 5,191,101 A | 3/1993 | Palazzotto et al. | 356/47 |
| 5,312,940 A | 5/1994 | Grubbs et al. | 556/135 |
| 5,342,909 A | 8/1994 | Grubbs et al. | 526/171 |
| 5,483,014 A | 1/1996 | Turner et al. | 526/113 |
| 5,504,049 A | 4/1996 | Crowther et al. | 502/117 |
| 5,710,298 A | 1/1998 | Grubbs et al. | 556/22 |
| 5,728,917 A | 3/1998 | Grubbs et al. | 585/653 |
| 5,750,815 A | 5/1998 | Grubbs et al. | 585/541 |
| 5,977,393 A | 11/1999 | Grubbs et al. | 556/31 |
| 6,121,395 A | 9/2000 | Turner | 526/134 |
| 6,124,509 A | 9/2000 | Voges et al. | 368/881 |
| 2002/0049136 A1 | 4/2002 | Kourtekis et al. | 502/308 |
| 2002/0058812 A1 | 5/2002 | Grubbs et al. | 546/2 |
| 2002/0137978 A1 | 9/2002 | Grubbs et al. | 585/507 |

OTHER PUBLICATIONS

Ojima et al., "Recent Advances In The Hydrosilylation and Related Reactions," *The Chemistry of Organic Silicon Compounds*, 2:1688–1792, Chapter 29 (1998).

Ojima, I., "The Hydrosilylation Reaction," *The Chemistry of Organic Silicon Compounds*, 1480–1526, Chapter 25 (1989).

Schmidt, T., "Molybdenum Oxadience Catalysts for the Chemoselective Hydrosilylation of α,β–Unsaturated Ketones and Aldehydes," *Tetrahedron Letters*, 35(21):3513–3516 (1994).

Hermann et al., "N–Heterocyclic Carbenes," *Agnew Chem. Int. Ed. Engl.*, 36:2162–2187 (1997).

Herrmann, W., "N–Heterocyclic Carbenes: A New Concept in Organometallic Catalysis," *Angew. Chem. Int. Ed.*, 41:1290–1309 (2002).

Reed, C., "Carboranes: A New Class of Weakly Coordinating Anions for Strong Electrophiles, Oxidants, and Superacids," *Acc. Chem. Res.*, 31:133–139 (1998).

Xie et al., "New Weakly Coordinating Anions 3:[†]Useful Silver and Trityl Salt Reagents of Carborane Anions," *J. Am. Chem. Soc.*, 116:1907–1913 (1994).

Berk et al., "An Air–Stable Catalyst System for the Conversion of Esters to Alcohols," *The Journal of Organic Chemistry*, 57(14):3751–3753 (1992).

Verdaguer et al., "Titanocene–Catalyzed Reduction of Lactones to Lactols," *J. Org. Chem.*, 62:8522–8528 (1997).

Barr et al., "Titanocene–Catalyzed Reduction of Esters Using Polymethylhydrosiloxane as the Stoichiometric Reductant," *J. Org. Chem.*, 59:4323–4326 (1994).

Mao et al., "Catalytic Hydrosilation of Organic Esters Using Manganese Carbonyl Acetyl Complexes, $(L)(CO)_4MnC(O)CH_3$ $(L=CO,PPh_3)$," *J. Am. Chem. Soc.*, 117:10139–10140 (1995).

*Primary Examiner*—Porfiro Nazario-Gonzalez
(74) *Attorney, Agent, or Firm*—Margaret C. Bogosian

(57) ABSTRACT

A compound is provided including an organometallic complex represented by the formula I:

$$[C_pM(CO)_2(NHC)L_k]^+A^-  \qquad I$$

wherein M is an atom of molybdenum or tangsten, Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radical, $C_{1-20}$ hydrocarbyl radical, substituted hydrocarbyl radical, halogen radical, halogen-substituted hydrocarbyl radical, —OR, —C(O)R', —CO$_2$R', —SiR'$_3$ and —NR'R", wherein R' and R" are independently selected from the group consisting of H radical, $C_{1-20}$ hydrocarbyl radical, halogen radical, and halogen-substituted hydrocarbyl radical, wherein said $Q^1$ to $Q^5$ radicals are optionally linked to each other to form a stable bridging group, NHC is any N-heterocyclic carbene ligand, L is either any neutral electron donor ligand, wherein k is a number from 0 to 1 or L is an anionic ligand wherein k is 2, and $A^-$ is an anion. Processes using the organometallic complex as catalyst for hydrogenation of aldehydes and ketones are provided. Processes using the organometallic complex as catalyst for the hydrosilylation of aldehydes, ketones and esters are also provided.

32 Claims, No Drawings

CATALYSTS FOR HYDROGENATION AND HYDROSILYLATION, METHODS OF MAKING AND USING THE SAME

This invention was made with Government support under contract number DE-AC02-98CH10886, awarded by the U.S. Department of Energy. The Government has certain rights in the invention.

BACKGROUND OF THE INVENTION

The present invention relates to catalysts for the homogenous hydrogenation or hydrosilylation of carbonyl compounds. More specifically, the invention relates to processes for the hydrogenation of ketones and aldehydes using organometallic complexes of tungsten (W) and molybdenum (Mo) as catalysts or catalyst precursors. The invention also relates to processes for the hydrosilylation of ketones, aldehydes and esters using the same catalysts or catalyst precursors.

Hydrogenation reactions involve the addition of hydrogen to an organic compound whereby, for example, a ketone can be reduced to an alcohol. Prior art processes have generally required the presence of a heterogeneous catalyst with a solid phase of platinum, rhodium, palladium or nickel along with relatively high hydrogen pressure and elevated temperature.

Other hydrogenation processes currently in use employ inexpensive Mo and W metals to hydrogenate ketones under mild conditions of temperature and pressure. However, a limitation encountered with these processes is the decomposition of the catalysts, due to dissociation of a phosphine ligand.

Hydrosilylation reactions involve the addition of hydrosilane to ketones, aldehydes, or esters to form primarily alkoxysilanes. Prior art hydrosilylation processes have also required rhodium, platinum or palladium complexes as catalysts.

Thus, traditional homogeneous catalysts for hydrogenation or hydrosilylation of ketones or aldehydes use precious metals such as platinum (Pt), rhodium (Rh), iridium (Ir) or ruthenium (Ru), which are expensive and, therefore, frequently uneconomical. In contrast, the catalysts of the present invention, which use either molybdenum (Mo) or tungsten (W), are prepared with less expensive metals, and, therefore, offer economic advantages.

SUMMARY OF THE INVENTION

The present invention relates to catalysts and processes that use the catalysts for the homogeneous catalytic hydrogenation of ketones and aldehydes to alcohols with $H_2$ as the stoichiometric redundant and organometallic tungsten (W) and molybdenum (Mo) complexes as the catalysts.

The present invention also relates to catalysts and processes for the hydrosilylation of ketones, aldehydes or esters, represented by the formulas $R(C=O)R^1$, $R(C=O)H$ or $R(CO_2)R^1$. The functional groups R and $R^1$ are selected from hydrogen, $C_{1-30}$ hydrocarbyl radicals and substituted-hydrocarbyl radicals, which can be the same or different.

The catalyst or catalyst precursor includes an organometallic complex represented by the formula I $$[CpM(CO)_2(NHC)L_k]^+A^- \qquad I$$

wherein M is a molybdenum or tungsten atom; Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radicals, hydrocarbyl radicals and substituted hydrocarbyl radicals, halogens (F, Cl, Br, I), halogen-substituted hydrocarbyl radicals, and radicals represented by the formulas —OR', —C(O)R', —CO$_2$R', —SiR'$_3$, —NR'R" wherein R' and R" are independently selected from the group consisting of H radicals, hydrocarbyl radicals, halogens, and halogen-substituted hydrocarbyl radicals, wherein further $Q^1$ to $Q^5$ radicals can be optionally linked to each other to form a stable bridging group; NHC is any N-heterocyclic carbene ligand, L is either any neutral electron donor ligand wherein k is a number from 0 to 1 or L is an anionic ligand wherein k is 2, and $A^-$ is an anion.

In an embodiment, the catalysts of the invention can be prepared by reacting a metal hydride represented by the formula II:

$$CpM(CO)_2(NHC)H \qquad II$$

with a hydride removing agent selected from $BR_3$ or a compound represented by formula $Y^+A^-$, wherein $Y^+$ is selected from the group consisting of $(aryl)_3C^+$, $(aryl)_2HC^+$, $C_7H_7^+$, $R_3NH^+$, $Ag^+$ and $(C_5R_5)_2Fe^+$, wherein R is a hydrocarbyl or substituted hydrocarbyl, $A^-$ is an anion selected from the group consisting of $BF_4^-$, $PF_6^-$, $SbF_6^-$, $CF_3SO_3^-$, $CB_{11}H_{12}^-$, $CB_9H_{10}^-$ $CB_9H_5X_5^-$; $CB_{11}H_6X_6^-$; wherein X is F Cl, Br or I, $HBR_3^-$, wherein R is hydrocarbyl or substituted hydrocarbyl, and $[(M')Z^1 Z^2 \ldots Z^n]^-$, M' is an element selected from atoms of group 13, n is the total number of Z ligands or n is 4, and $Z^1$ to $Z^n$ are independently selected from the group consisting of H radical, $C_{1-20}$ hydrocarbyl radical, substituted hydrocarbyl radical, halogens, halogen-substituted hydrocarbyl radical, hydrocarbyl-, halogen-substituted hydrocarbyl organometalloid radical, —OR, —C(O)R', —CO$_2$R', and —NR'R", wherein R' and R" are independently selected from the group consisting of H radicals, $C_{1-20}$ hydrocarbyl radical, halogens, and halogen-substituted hydrocarbyl radical; $Z^1$ to $Z^n$ radicals can be optionally linked to each other to form a stable bridging group. In the metal hydride of formula II, Cp, M and NHC are as described herein above.

The process for catalytic hydrogenation includes contacting an organic compound which contains at least one reducible functional group selected from the group consisting of $R(C=O)R^1$ and $R(C=O)H$, wherein R and $R^1$ are each independently selected from hydrogen (H) or any $C_1$–$C_{20}$ hydrocarbyl or substituted-hydrocarbyl radical with hydrogen in the presence of a catalyst to form a reaction mixture, wherein the catalyst comprises an organometallic complex described above and represented by the formula:

$$[CpM(CO)_2(NHC)L_k]^+A^- \qquad I$$

wherein Cp, M, NHC, $L_k$ and $A^-$ are as described hereinbelow.

The process for catalytic hydrosilylation includes contacting an organic compound which contains at least one functional group selected from the group consisting of $R(C=O)R^1$, $R(C=O)H$, and $R(CO_2)R^1$, wherein R and $R^1$ are each independently selected from hydrogen (H) or any $C_1$–$C_{30}$ hydrocarbyl or substituted-hydrocarbyl radical in the presence of hydrosilane with a catalyst to form a mixture, wherein the catalyst comprises an organometallic complex described above and represented by the formula:

$$[CpM(CO)_2(NHC)L_k]^+A^- \qquad I$$

wherein Cp, M, NHC, $L_k$ and $A^-$ are as described hereinbelow.

The hydrogenation process is carried out in the presence of hydrogen at a pressure from 1 atmosphere to 5000 psi, and at a temperature of from −95° C. to 120° C. Preferably, the pressure is from about 1 atmosphere to about 800 psi and the temperature is from 20° C. to 100° C. The hydrosilylation process is carried out at a temperature from about −95° C. to about 120° C. and, in one aspect of the invention, from about 20° C. to about 100° C.

As a result of the present invention catalysts are provided with significantly higher lifetime and increased thermal stability. Moreover, the homogeneous organometallic Mo and W complexes of the present invention provide an effective hydrogenation or hydrosilylation catalyst at a considerably reduced cost over the prior art catalysts that use Pt, Rh, Ir or Ru complexes.

DETAILED DESCRIPTION OF THE INVENTION

The present invention relates broadly to catalysts or catalyst precursors used for a variety of hydrogenation or hydrosilylation reactions.

Catalysts

The active catalyst of the present invention is an organometallic complex represented by the formula:

$$[CpM(CO)_2(NHC)L_k]^+A^-  \qquad \text{I}$$

wherein M is a molybdenum or tungsten atom; Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radicals, hydrocarbyl radicals and substituted hydrocarbyl radicals, halogens (F, Cl, Br, I), halogen-substituted hydrocarbyl radicals, and radicals represented by —OR', —C(O)R', —CO$_2$R', —SiR'$_3$, —NR'R", wherein R' and R" are independently selected from the group consisting of H radicals, hydrocarbyl radicals, halogens, and halogen-substituted hydrocarbyl radicals), wherein $Q^1$ to $Q^5$ radicals can be linked to each other through a stable bridging group, NHC is any N-heterocyclic carbene ligand, L is either any neutral electron donor ligand, wherein k is a number from 0 to 1, or L is an anion ligand wherein k is 2, and A$^-$ is an anion. NHC can be an unsubstituted or substituted N-heterocyclic carbene selected from the group consisting of carbenes represented by formula III

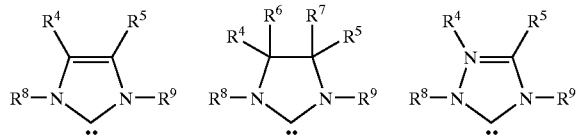

III wherein $R^4$, $R^5$, $R^6$, $R^7$, $R^8$ and $R^9$ are each independently hydrogen, halogen or a substituent selected from the group consisting of C$_1$–C$_{20}$ alkyl, C$_2$–C$_{20}$ alkenyl, C$_2$–C$_{20}$ alkynyl, aryl, C$_1$–C$_{20}$ carboxylate, C$_1$–C$_{20}$ alkoxy, C$_2$–C$_{20}$ alkenyloxy, C$_2$–C$_{20}$ alkynyloxy, aryloxy, C$_2$–C$_{20}$ alkoxycarbonyl, C$_1$–C$_{20}$ alkylthiol, aryl thiol, C$_1$–C$_{20}$ alkylsulfonyl and C$_1$–C$_{20}$ alkylsulfinyl. Further, each of the $R^4$, $R^5$, $R^6$, $R^7$, $R^8$ and $R^9$ radicals can be optionally substituted with one or more moieties selected from the group consisting of C$_1$–C$_{20}$ hydrocarbyl, C$_1$–C$_{20}$ alkoxy, and other functional groups, examples of which include but are not limited to hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen, wherein $R^4$, $R^5$, $R^6$, $R^7$, $R^8$ and $R^9$ radicals are optionally linked to each other to form a stable bridging group. In the metal hydride or formula II, Cp, M and NHC are as described herein above.

The inclusion of an NHC ligand in the Mo and W catalysts of the invention has been found to improve the catalytic activity of these organometallic complexes.

In another aspect of the invention, the N-heterocyclic carbene ligand is 1,3-bis(2, 4,6-trimethylphenyl)-imidazol-2-ylidene (IMes).

When NHC is IMes the catalysts of the present invention are represented by the following formula:

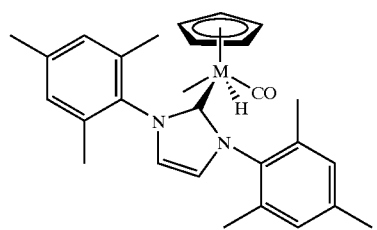

IV wherein M is Mo or W.

The NHC ligands described above are easily obtained in accordance with methods well known in the art such as are described by Herrmann et al. in "N-Heterocyclic Carbenes," Angew. Chem. Int. Ed, 36, 2162–2187, (1997) and Herrmann et al. in "N-Heterocyclic Carbenes: A New Concept in Organometallic Catalysts," Angew. Chem. Int. Ed., 41, 1290–1309, (2002).

In an embodiment, L can be selected from the group consisting of a hydrocarbon or halogenated hydrocarbon solvent molecule, a dihydrogen (H$_2$) or dihydride (H$^-$)$_2$, a ketone or aldehyde substrate, a product alcohol molecule and mixtures thereof.

In another embodiment, L can be selected from the group consisting of a hydrocarbon or halogenated hydrocarbon solvent molecule, a dihydrogen (H$_2$) or hydrosilane, a ketone, an aldehyde or an ester substrate, an alkoxysilane, ether, or alcohol product molecule and mixtures thereof, or any combination of two anionic ligands such as hydride (H$^-$) and silyl (SiR$^{10}$R$^{11}$R$^{12}$)$^-$ and mixtures thereof, wherein R$^{10}$, R$^{11}$, R$^{12}$ are independently hydrogen, halogen or a substituent selected from the group consisting of C$_1$–C$_{20}$ alkyl, C$_2$–C$_{20}$ alkenyl, C$_2$–C$_{20}$ alkynyl, aryl, C$_1$–C$_{20}$ carboxylate, C$_1$–C$_{20}$ alkoxy, C$_2$–C$_{20}$ alkenyloxy, C$_2$–C$_{20}$ alkynyloxy, aryloxy, C$_2$–C$_{20}$ alkoxycarbonyl, C$_1$–C$_{20}$ alkylthiol, aryl thiol, C$_1$–C$_{20}$ alkylsulfonyl and C$_1$–C$_{20}$ alkylsulfinyl, wherein further each R$^{10}$, R$^{11}$, R$^{12}$ is optionally substituted with one or more moieties selected from the group consisting of C$_1$–C$_{20}$ hydrocarbyl, C$_1$–C$_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen.

For purposes of this invention, the term "hydrocarbon" refers to all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted having C$_{1-30}$ for nonaromatic organic compounds and C$_{3-36}$ for aromatic organic compounds.

As used herein, the term "hydrocarbyl" refers to univalent groups formed by removing a hydrogen atom from a hydrocarbon having 1–30 carbons.

As used herein, the term "substituted" includes all permissible substituents of organic compounds unless otherwise indicated In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 30. The permissible substituents can be one or more and the same or different for appropriate organic compounds. This invention is not intended to be limited in any manner by the permissible substituents of organic compounds.

As used herein, the term "aryl" refers to an aromatic cyclic structure containing at least one monocyclic carbon ring including without limitation phenyl, naphthyl, anthracenyl and the like. "Substituted aryl" refers to an aryl group substituted with substituents as defined hereinabove.

Anion ($A^-$) can be selected from the group consisting of $HBR_3^-$, wherein R is a hydrocarbyl or substituted hydrocarbyl, $BF_4^-$, $PF_6^-$, $SbF_6^-$, $CF_3SO_3^-$, $CB_{11}H_{12}^-$, $CB_9H_{10}^-$, $CB_9H_5X_5^-$, $CB_{11}H_6X_6^-$, wherein X is F, Cl, Br and I, and $[(M')Z^1 Z^2 \ldots -Z^n]^-$ wherein, M' is an element selected from the atoms of group 13; n is the total number of Z ligands, and $Z^1$ to $Z^n$ are independently selected from the group consisting of H radicals, $C_1$–$C_{20}$ hydrocarbyl radicals and substituted hydrocarbyl radicals, halogens (F, Cl, Br, I), halogen-substituted hydrocarbyl radicals, hydrocarbyl- and halogen-substituted hydrocarbyl organometalloid radicals, and radicals represented by the formulas —OR', —C(O)R', —CO$_2$R', —NR'R", wherein R' and R" are independently selected from the group consisting of H radicals, $C_1$–$C_{20}$ hydrocarbyl radicals, halogens, and halogen-substituted hydrocarbyl radicals; $Z^1$ to $Z^n$ radicals can be optionally linked to each other to form a stable bridging group. In another aspect, the total number of Z ligands is four.

M' can be any metal of group 13 of the Periodic Table of Elements as published by CRC Press, Inc., 1984 including but not limited to boron, aluminum or gallium. $Z^1$ to $Z^n$ are each fluorine substituted phenyl, naphtyl or anthracenyl radicals.

In another embodiment, the catalyst of the present invention can further include a solvent of crystallization thereby forming $[CpW(CO)_2 (NHC)L_k]^+[A]^-.Y'_h$, wherein h is a number from 0 to 1 and Y' is selected from the group consisting of any hydrocarbon, aromatic hydrocarbon, halocarbon, or ether, examples of which include but are not limited to hexane, benzene, toluene, tetrahydrofuran, diethyl ether and mixtures thereof.

The catalysts of the present invention have novel and valuable properties. For example, a stability at room temperature (about 23° C.) and a useful combination of solubility properties allows the use of the catalyst in "neat" reagents, i.e., in the absence of a solvent. Another characteristic is that whenever the substrates do not have aromatic groups, the catalysts precipitate upon completion of the hydrosilylation reaction, and can be efficiently recovered from the reaction mixtures and reused. Thus many catalysts of the present invention are recyclable.

Method of Making the Catalysts

The catalysts of the present invention are prepared by reacting a metal hydride represented by the formula CpM(CO)$_2$(NHC)H with a hydride removing agent selected from BR$_3$ or a compound represented by formula $Y^+A^-$, wherein $Y^+$ is selected from the group consisting of $(aryl)_3C^+$, $(aryl)_2HC^+$, $C_7H_7^+$, $R_3NH^+$, $Ag^+$ and $(C_5R_5)_2Fe^+$, wherein R is a hydrocarbyl radical or substituted hydrocarbyl radical, $A^-$ is all anion selected from the group consisting of $BF_4^-$, $PF_6^-$, $SbF_6^-$, $CF_3SO_3^-$, $CB_{11}H_{12}^-$, $CB_9H_{10}^-$, $CB_9H_5X_5^-$, $CB_{11}H_6X_6^-$, wherein X is F, Cl, Br or I, $HBR_3^-$, wherein R is a hydrocarbyl radical or subsubstituted hydrocarbyl radical, and $[(M')Z^1 Z^2 \ldots Z^n]^-$, M' is an element selected from atoms of group 13, n is the total number of Z ligands or n is 4, and $Z^1$ to $Z^n$ are independently selected from the group consisting of H radical, $C_{1-20}$ hydrocarbyl radical, substituted hydrocarbyl radical, halogens, halogen-substituted hydrocarbyl radical, hydrocarbyl-, halogen-substituted hydrocarbyl organometalloid radical, —OR, —C(O)R', —CO$_2$R', and —NR'R", wherein R' and R" are independently selected from the group consisting of H radicals, $C_{1-20}$ hydrocarbyl radical, halogens, and halogen-substituted hydrocarbyl radical; said $Z^1$ to $Z^n$ radicals optionally linked to each other to form a stable bridging group.

In one aspect, the hydride removing agent is $Ph_3C^+A^-$, wherein Ph is $C_6H_5$ and $A^-$ is an anion as described hereinabove.

The metal hydride represented by the formula CpM(CO)$_2$(NHC)H is prepared by reacting a metal phosphine hydride represented by the formula CpM(CO)$_2$(PR$_3$)H, wherein R is any $C_1$–$C_{20}$ alkyl or $C_6$–$C_{36}$ aryl group and combination thereof with NHC, which is as described herein above.

The active catalyst can be prepared prior to being mixed with the organic compound that is being hydrogenated or hydrosilylated, or it can be generated in the reaction mixture. When the catalyst is prepared in the reaction mixture, the metal hydride can be mixed with the hydride removing agent.

Method of Using the Organometallic Complexes

The organometallic complexes of the present invention can be used broadly as catalysts for hydrogenation or hydrosilylation reactions.

The present invention provides a process for hydrogenating of ketones and aldehydes to alcohols using organometallic molybdenum and tungsten complexes as catalysts. Using the process of this invention, unsaturated organic compounds can be hydrogenated to give the corresponding saturated derivatives. Organic compounds which may be hydrogenated in accordance with the present invention include but are not limited to ketones and aldehydes.

In an aspect, the organic compound that is hydrogenated can be represented by at least one reducible functional group selected from the group consisting of $R^1(C=O)R^2$ and $R^1(C=O)H$, wherein $R^1$ and $R^2$ are each independently selected from any $C_1$–$C_{20}$ hydrocarbyl group. The hydrogenation of ketones and aldehydes involves the overall addition of two hydrogen atoms to the carbon-oxygen double bond to result in the formation of the corresponding alcohol.

The hydrogenation process of the invention includes contacting aldehydes or ketones with hydrogen in the presence of the organometallic catalyst of the invention that is represented by the formula I:

$$[C_pM(CO)_2(NHC)L_k]^+A^- \qquad \text{I}$$

wherein M is a molybdenum or tungsten atom, Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radicals, $C_1$–$C_{20}$ hydrocarbyl radicals and substituted hydrocarbyl radicals halogens (F, Cl, Br, I), halogen-substituted hydrocarbyl radicals, and radicals represented by the formulas —OR', —C(O)R', —CO$_2$R', —SiR'$_3$, —NR'R", wherein R' and R" are independently selected from the group consisting of H radicals, hydrocarbyl radicals, halogens, and halogen-substituted hydrocarbyl radicals, said $Q^1$ to $Q^5$ radicals can optionally be linked to each other to form a stable bridging group; NHC is any N-heterocyclic carbene ligand, L is either any neutral electron donor ligand, k is a number from 0 to 1 or L is an anionic ligand, wherein k is 2, and (A⁻) is an anion as described hereinabove.

NHC can be an unsubstituted or substituted N-heterocyclic carbene as was more specifically described hereinabove. In an embodiment NHC can be IMes.

In a hydrogenation process, L can be selected from the group consisting of a hydrocarbon or halogenated hydrocarbon solvent molecule, a dihydrogen (H$_2$) or dihydride (H⁻)$_2$, a ketone or aldehyde substrate, a product alcohol molecule and mixtures thereof.

Anion (A⁻) can be selected from the group consisting of $BF_4^-$, $PF_6^-$, $SbF_6^-$, $CF_3SO_3^-$, $CB_{11}H_{12}^-$, $CB_9H_{10}^-$, $CB_9H_5X_5^-$, $CB_{11}H_6X_6^-$, wherein X is F, Cl, Br or I, $HBR_3^-$, wherein R is a hydrocarbyl radical or substituted hydrocarbyl radical, and $[(M')Z^1 Z^2 ... Z^n]^-$ as was more specifically described hereinabove.

The present invention also provides a process for hydrosilylation of ketones, aldehydes and esters to alkoxysilanes, ethers or alcohols using organometallic molybdenum and tungsten complexes of the invention as the catalysts. The organic compound that can be hydrosilylated contains at least one reducible functional group selected from the group consisting of $R(C=O)R^1$, $R(C=O)H$ or $R^1(CO_2)R^2$, wherein $R^1$ and $R^2$ are each independently selected from hydrocarbyl radicals or substituted-hydrocarbyl radicals, which can be the same or different.

The hydrosilylation process includes contacting aldehydes, ketones or esters with hydrosilanes in the presence of the organometallic catalyst of the present invention as described herein above.

In a hydrosilylation process, L can be selected from the group consisting of a hydrocarbon or halogenated hydrocarbon solvent, a dihydrogen (H$_2$) or hydrosilane, a ketone, an aldehyde or an ester substrate, an alkoxysilane, ether, or alcohol product molecule and mixtures thereof, or any combination of two anionic ligands such as hydride (H⁻) and silyl (SiR$^{10}$R$^{11}$R$^{12}$)⁻, wherein R$^{10}$, R$^{11}$ and R$^{12}$ are each independently hydrogen, halogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein further each R$^{10}$, R$^{11}$, R$^{12}$ is optionally substituted with one or more moieties selected from the group consisting of $C_1$–$C_{20}$ hydrocarbyl, $C_1$–$C_{20}$ alkoxy, hydroxyl, thiol, thioether, ketone, aldehyde, ester, ether, amine, imine, amide, nitro, carboxylic acid, disulfide; carbonate, isocyanate, carbodiimide, carboalkoxy; carbamate and halogen.

Hydrosilylation of ketone is of synthetic interest because when followed by hydrolysis of the resulting alkoxysilane, this reaction provides a mild route for reducing ketones to secondary alcohols.

The hydrogenation and hydrosilylation processes of the present invention can be carried out over a wide range of temperatures and pressures. For example, the pressure of hydrogen in the hydrogenation reactions can vary over a range from about 1 atmosphere to about 5,000 psi, the temperature can vary over a range from −95° C. to about 120° C. Nevertheless, the processes of the present invention can be conducted under mild conditions of temperatures and pressures including without limitations 1 atmosphere and room temperature of about 23° C. In certain embodiments the pressure can range from about 1 atmosphere to about 800 psi and the temperature from about 20° C. to about 100° C. The temperature range for hydrosilylation reactions is from about −95° C. to about 120° C. and, in another aspect of the invention, from about 20° C. to about 100° C.

Various solvents may be used with the inventive methods of hydrogenation or hydrosilylation.

Any solvent which is chemically inert, which does not interfere with the hydrogenation or hydrosilylation reaction and which at least partially dissolves the catalyst may be employed. The solvents can be aromatics such as toluene, xylene, mesitylene and benzene or halogenated aromatics and other well known solvents such as hexane, tetrahydrofuran and diethyl ether. If the reactants are mutually soluble, the use of a solvent is not necessary and the catalysts can catalyze the reaction in the absence of a solvent as "neat" reagents. In addition, the substrate, either a ketone, aldehyde or ester, can be partially soluble or it can be completely soluble in the solvent.

The active catalyst can be prepared prior to being mixed with the organic compound that is being hydrogenated or hydrosilylated and it can also be generated in the reaction mixture. When the catalyst is prepared in the reaction mixture, the metal hydride is mixed with hydride removing agent as described hereinabove.

The processes of the invention can be conducted in any type of apparatus that enables intimate contact of the reactants and control of operating conditions. The hydrogenated product may be removed by known means such as distillation and/or chromatography.

EXAMPLES

The following non-limiting examples are illustrative of the present invention. It should be noted that various changes could be made in the examples and processes therein without departing from the scope of the present invention. For this reason, it is intended that the embodiments of the present application should be interpreted as being illustrative and not limiting in any sense.

Instrumentation

All operations were performed in Schlenk-type glassware on a dual-manifold Schlenk line or in a argon-filled Vacuum Atmospheres glovebox. NMR spectra were obtained on Bruker Avance-400 FT NMR spectrometer (400 MHz for $^1$H). All NMR spectra were recorded at 25° C. unless stated otherwise. Chemical shifts for $^1$H and $^{13}$C NMR spectra were referenced using internal solvent resonances and are reported relative to tetramethylsilane. External standards of trifluorotoluene (set as δ=−63.73) and 85% $H_3PO_4$ (set as δ=0) were used for referencing 19F and $^{31}$P NMR spectra. $^{13}$C{$^1$H} and $^{31}$P{$^1$H} NMR spectra were recorded with broadband $^1$H decoupling unless stated otherwise. For quantitative $^1$H NMR measurements the relaxation delay was set at 30 seconds. GC-MS spectra were recorded on an Agilent Technologies 5973 mass selective detector connected to an Agilent Technologies 6890N gas chromatograph equipped with an HP-5 ms column (5% phenyldimethylpolysiloxane).

Infrared spectra were recorded on a Mattson Polaris spectrometer. Elemental analyses were performed by Schwarzkopf Microanalytical Laboratory, Inc. (Woodside. N.Y.).

Turnover Measurement

In the experiments described below turnovers is the number of moles of a carbonyl compound hydrogenated or hydrosilylated per mole of catalyst.

For example, in the hydrogenation of 3-pentanone the total turnover number [TON(total)] includes the alcohol (3-pentanol) formed by hydrogenation of the ketone, plus the ether $(Et_2CH)_2O$ formed through condensation of two molar equivalents of the alcohol. Each equivalent of ether is counted as representing two hydrogenation equivalents (or turnovers of the catalyst), since it takes two alcohols to form one ether.

For hydrosilylation reactions turnover numbers for every product are reported separately. Each equivalent of an ether (R(R')HCOCH(R')R) formed in a hydrosilylation of a ketone (R(R')C=O) is counted as representing two turnovers of the catalyst, since it takes two ketones to form one ether. However, each equivalent of an ether $(RCH_2OR')$ formed in a hydrosilylation of an ester $(RCO_2R')$ is counted as representing one turnover of the catalyst, since it takes one ester to form one ether. Each equivalent of an alkoxysilane $(RCH_2OSiEt_3$ or $R'OSiEt_3)$ formed in a hydrosilylation of an ester $(RCO_2R')$ is counted as representing 0.5 turnover of the catalyst, since it takes one ester to form two alkoxysilanes.

Examples 1 to 9 describes the syntheses of catalysts and catalyst precursors. Many of the materials used in Examples 1 to 9 are readily commercially available. Others such as $CpMo(CO)_2(PPh_3)H$ and $CpW(CO)_2(PPh_3)H$ are easily prepared by procedures available in scientific publications such as described by Bainbridge, A., et al., *J. Chem. Soc.* (A), 2715 (1968) and Kalck, P., et al., *J. Organomet. Chem*, 24, 445 (1970), respectively. Examples 10 to 18 describe the use of these catalysts and catalyst precursors in hydrogenation and hydrosilylation processes.

EXAMPLE 1

Synthesis of $CpMo(CO)_2(IMes)H$ from $CpMo\ (CO)_2(PPh_3)H$

For this example, $CpMo(CO)_2(PPh_3)H$ (480.0 mg, 1.000 mmol), IMes (306.0 mg, 1.000 mmol), and 10 mL of toluene were placed in a glass tube placed in a glove box. The glass tube was equipped with a teflon valve. The light yellow solids dissolved to produce a dark purple mother liquor. A new lightly colored precipitate formed almost immediately. The glass tube was heated at 95° C. for 3 hours. The product was recrystallized from toluene-hexanes (1:3) to yield 449 mg (86%) of pure $CpMo(CO)_2(IMes)H$ as light yellow crystals. The product had the following identification data:

$^1H$ NMR (THF-$d_8$) δ 7.16 (s, 2H, =CH), 7.02 (s, 4H, m-H-Mes), 4.62 (s, 5H, Cp), 2.34 (s, 6H, p-Me-Mes), 2.09 (s, 12H, o-Me-Mes), −4.73 (s, 1H, MoH). $^{13}C$ NMR (THF-$d_8$) δ 243.3 (d, $^2J_{CH}$=11 Hz, Mo-CO), 200.2 (d, $^2J_{CH}$=12 Hz, NCN), 139.5 (m, i-Mes), 139.2 (q, $^2J_{CH}$=6 Hz, p-Mes), 136.9 (q, $^2J_{CH}$=6 Hz, o-Mes), 130.0 (dm, $^1J_{CH}$=156 Hz, m-Mes), 124.3 (dd, $^1J_{CH}$=196 and $^2J_{CH}$=12 Hz, =CH), 89.0 (dp, $^1J_{CH}$=174 and $J_{CH}$=6 Hz, Cp), 21.2 (qt, $^1J_{CH}$=126 and $^3J_{CH}$=4 Hz, p-Me-Mes), 18.8 (qm, $^1J_{CH}$=128 Hz, o-Me-Mes). IR (THF-$d_8$)ν(CO)=1918 (vs) and 1843 (vs) cm$^{-1}$. IR (hexanes)ν(CO)=1930 (vs) and 1858 (vs) cm$^{-1}$. Analasys calculated for $C_{28}H_{30}N_2O_2Mo$: C, 64.37; H, 5.79; N, 5.36. Found: C, 64.13; H, 6.05; N, 5.34.

EXAMPLE 2

Synthesis of cis-$CpW(CO)_2(IMes)H$ from $CpW(CO)_2(PPh_3)H$

In a glove box, $CpW(CO)_2(PPh_3)H$ (608 mg, 1.07 mmol), IMes (333 mg, 1.09 mmol), and 3 mL of toluene were placed in a glass tube equipped with a teflon valve. The yellow solids dissolved to produce a brown-red mother liquor. A new lightly colored precipitate formed within 10–20 minutes. The color faded slowly to yellow-gray, indicating completion of the reaction after two days at 23° C. The product was washed with 2×7 mL of hexanes and recrystallized from toluene-hexanes (1:1) to yield 568 mg (87%) of pure $CpW(CO)_2(IMes)H$ as light yellow crystals. The product was identified by comparison to an authentic sample of $CpW(CO)_2(IMes)H$, which was synthesized by an independent route. The product had the same identification data as set forth in Example 3 hereinbelow.

EXAMPLE 3

Synthesis of $CpW(CO)_2(IMes)H$ from $CpW(CO)_2(PMe_3)H$

In a glovebox, $CpW(CO)_2(PMe_3)H$ (346.0 mg, 0.900 mmol), IMes (275.0 mg, 0.900 mmol), and 1 mL of toluene were placed in a glass tube equipped with a teflon valve. The light yellow solids dissolved to produce a dark purple mother liquor. A new lightly colored precipitate formed almost immediately. The volatiles were removed in vacuo, and the residue was heated in dynamic vacuo for 10 minutes at 120° C. The product was recrystallized from toluene-hexanes (1:1) to yield 416 mg (76%) of pure $CpW(CO)_2(IMes)H$ as light yellow crystals with 0.5 equivalents of crystallization solvent $(C_6H_5CH_3)$ Per W. The product had the following identification data:

$^1H$ NMR $(C_6D_6)$ δ 6.80 (s, 4H, m-H-Mes), 6.19 (s, 2H, =CH), 4.60 (s, 5H, Cp), 2.12 (s, 6H, p-Me-Mes), 2.10 (s, 12H, o-Me-Mes), −5.93 (s, $^1J_{WH}$=45 Hz, 1H, WH). $^1H$ NMR (THF-$d_8$, −100° C.) δ 7.40 (s, 2H, =CH), 7.06 (s, 4H, m-H-Mes), 4.71 (s, 5H, Cp), 2.34 (s, 6H, p-Me-Mes), 2.12 (br s, 6H, o-Me-Mes), 2.01 (br s, 6H, o-Me-Mes), −6.43 (s, $^1J_{WH}$=45 Hz, 1H, WH). $^{13}C$ NMR $(C_6D_6)$ δ 238.1 (m, W-CO), 184.1 (d, $^2J_{CH}$=14.8 Hz, NCN), 139.1 (m, i-Mes), 138.9 (q, $^2J_{CH}$=6 Hz, p-Mes), 136.6 (q, $^2J_{CH}$=6 Hz, o-Mes), 129.9 (dm, $^1J_{CH}$=157 Hz, m-Mes), 122.9 (dd, $^1J_{CH}$=195 and $^2J_{CH}$=12 Hz, =CH), 87.4 (d quintet, $^1J_{CH}$=177 and $J_{CH}$=7 Hz, Cp), 21.4 (qt, $^1J_{CH}$=126 and $^3J_{CH}$=5 Hz, p-Me-Mes), 19.1 (qm, $^1J_{CH}$=127 Hz, o-Me-Mes). $^{13}C\{^1H\}$ NMR (THF-$d_8$, −100° C.) δ 247.4 (br s, W-CO), 232.3 (br s, W-CO), 181.5 (s, NCN), 139.4 (s, p-Mes or i-Mes), 138.9 (s, p-Mes or i-Mes), 137.1 (br s, o-Mes), 136.6 (br s, o-Mes), 129.8 (br s, m-Mes), 124.1 (br s, =CH), 88.0 (s, Cp), 21.3 (br s, p-Me-Mes), 19.4 (br s, o-Me-Mes), 18.9 (br s, o-Me-Mes). IR (toluene)ν(CO)=1915 (vs) and 1824 (vs) cm$^{-1}$. IR $(CD_2Cl_2)$ν(CO)=1906 (vs) and 1810 (vs) cm$^{-1}$. Analysis calculated for $C_{31.5}H_{34}N_2O_2W$ (with 0.5 equiv. of crystallization solvent, $C_6H_5CH_3$, per W): C, 57.63; H, 5.22; N, 4.27. Found: C, 57.52; H, 5.07; N, 4.14.

EXAMPLE 4

Synthesis of $[CpMo(CO)_2(IMes)]^+[B(C_6F_5)_4]^-.0.5\ CH_3Ph$

For this example, $CpMo(CO)_2(IMes)H$ (52.4 mg, 0.100 mmol) was added slowly to a stirred solution of $Ph_3C^+B(C_6F_5)_4^-$ (96.6 mg, 0.105 mmol) in 5 mL of toluene in a glass tube contained in a glovebox. The tube was equipped with a teflon valve. A dark purple precipitate formed. The stirring was continued for 40 minutes. The bright yellow mother liquor was discarded, and the precipitate was washed with toluene until the washings were colorless (5×3 mL). The product was washed with hexanes (3×3 mL) and dried in vacuo to yield 112 mg (87%) of dark purple crystals of pure $CpMo(CO)_2(IMes)^+B(C_6F_5)_4^-$ with 0.5 equivalents of crystallization solvent ($C_6H_5CH_3$) per Mo. The product was insoluble in common non-coordinating NMR solvents. IR (Nujol)ν(CO)=1999 (vs) and 1905 (vs) $cm^{-1}$. Analysis Calculated for $C_{55}H_{33}BF_{20}N_2O_2Mo$ including 0.5 equivalents of crystallization solvent. $C_6H_5CH_3$, per Mo was: C, 53.47; H, 2.67; N, 2.25. We found the following: C, 53.18; H, 2.77; N, 2.43.

The identification data of the product in THF-$d_8$ for cis-$[CpMo(CO)_2(IMes)(THF-d_8)]^+[B(C_6F_5)_4]^-$ was as follows: $^1$H NMR (THF-$d_8$) δ 7.83 (s, 2H, =CH), 7.13 (s, 4H, m-H-Mes), 5.14 (s, 5H, Cp), 2.36 (s, 6H, p-Me-Mes), 2.11 (s, 12H, o-Me-Mes). $^{13}C\{^1H\}$ NMR (THF-$d_8$) δ 251 (m, Mo-CO), 187.3 (s, NCN), 149.3 (dm, $^1J_{CF}$=246 Hz, o-$C_6F_5$), 141.0 (br s, p-Mes or i-Mes), 139.2 (dm, $^1J_{CF}$=243 Hz, p-$C_6F_5$), 137.4 (br s, p-Mes or i-Mes), 137.2 (dm, $^1J_{CF}$=244 Hz, m-$C_6F_5$), 136.5 (br s, o-Mes), 130.3 (br s, m-Mes), 127.6 (br s, =CH), 125 (br m, i-$C_6F_5$), 96.9 (s, Cp), 21.0 (s, p-Me-Mes), 18.7 (br s, o-Me-Mes). $^{19}$F NMR (THF-$d_8$) δ −132.9 (d, 8F, $^3J_{FF}$=10 Hz, o-$C_6F_5$), −165.1 (t, 4F, $^3J_{FF}$=21 Hz, p-$C_6F_5$), −168.6 (t, 8F, $^3J_{FF}$=18 Hz, m-$C_6F_5$). IR (THF) ν(CO)=1977 (vs) and 1882 (vs) $cm^{-1}$.

EXAMPLE 5

Synthesis of $[CpW(CO)_2(IMes)]^+[B(C_6F_5)_4]^-\cdot CH_3Ph$

In a glovebox, $CpW(CO)_2(IMes)H$ (244.0 mg, 0.400 mmol) was added slowly to a stirred solution of $Ph_3C^+B(C_6F_5)_4^-$ (387.0 mg, 0.420 mmol) in 10 mL of toluene in a glass tube equipped with a teflon valve. A dark purple precipitate formed. The stirring was continued for 30 minutes. The bright yellow mother liquor was discarded, and the precipitate was washed with toluene until the washings were colorless (5×3 mL). The product was washed with hexanes (3×3 mL) and dried in vacuo to yield 490 mg (91%) of dark purple crystals of $CpW(CO)_2(Mes)^+B(C_6F_5)_4^-$ with 1 equivalent of crystallization solvent ($C_6H_5CH_3$) per W. The product was insoluble in common non-coordinating NMR solvents. IR (Nujol)ν(CO)=1980 (vs) and 1890 (vs) $cm^{-1}$. IR ($CF_3Ph$)ν(CO)=1983 (vs) and 1900 (vs) $cm^{-1}$. Analysis calculated for $C_{59}H_{37}BF_{20}N_2O_2W$ was: C, 51.33; H, 2.70; N, 2.03. We found the following: C, 51.24; H, 3.35; N, 2.02.

The identification data of the product in THF-$d_8$ for cis-$[CpW(CO)_2(Mes)(THF-d_8)]^+[B(C_6F_5)_4]^-$ was as follows: $^1$H NMR (THF-$d_8$, −30° C.) δ 7.99 and 7.87 (d, $^1J_{HH}$=2 Hz, 1H, =CH), 7.26, 7.19, 7.16, and 7.03 (s, 1H, m-H-Mes), 5.36 (s, 5H, Cp), 2.41, 2.31, 2.30, 2.23, 2.14, and 2.02 (s, 3H, p-Me-Mes and o-Me-Mes). $^{13}C\{^1H\}$ NMR (THF-$d_8$, −40° C.) δ 247.1 and 246.2 (s, W-CO), 179.6 (s, NCN), 149.0 (br d, $^1J_{CF}$=240 Hz, o-$C_6F_5$), 141.3 and 140.0 (s, p-Mes or i-Mes), 139.1 (dm, $^1J_{CF}$=242 Hz, p-$C_6F_5$), 137.9 (s, p-Mes or i-Mes), 137.0 (dm, $^1J_{CF}$=244 Hz, m-$C_6F_5$), 137.5, 136.7, 136.5, and 135.8 (s, o-Mes), 130.7, 130.3, 130.2, and 129.4 (s, m-Mes), 128.4 and 126.6 (br s, =CH), 125 (br m, i-$C_6F_5$), 95.4 (s, Cp), 21.1 and 21.0 (s, p-Me-Mes), 19.7, 18.9, 18.7, and 18.6 (s, o-Me-Mes). $^{19}$F NMR (THF-$d_8$, −30° C.) δ −133.5 (d, 8F, $^3J_{FF}$=11Hz, o-$C_6F_5$), −164.9 (t, 4F, $^3J_{FF}$=21 Hz, p-$C_6F_5$), −168.5 (t, 8F, $^3J_{FF}$=18 Hz, m-$C_6F_5$). IR (THF-$d_8$)ν(CO)=1962 (vs) and 1859 (vs) $cm^{-1}$.

EXAMPLE 6

Synthesis of $[CpW(CO)_2(IMes)(H)_2]^+[B(C_6F_5)_4]^-$

In a glovebox, $[CpW(CO)_2(IMes)(CH_3Ph)]^+[B(C_6F_5)_4]^-$ (70 mg, 0.051 mmol) placed in an NMR tube equipped with a teflon valve. The tube was taken out of the glovebox, and THF-$d_8$ was vacuum transferred into the tube, producing a dark purple solution. The tube was then filled with about 1.1 atm $H_2$ at −196° C., sealed, and warmed to room temperature. It was shaken for 3 minutes at room temperature and used for low temperature NMR measurements. The sample was found to contain $[CpW(CO)_2(IMes)(THF-d_8)]^+[B(C_6F_5)_4]^-$ and two isomers of $[CpW(CO)_2(IMes)(H)_2]^+[B(C_6F_5)_4]^-$. The identification data of these isomers was as follows:

Major isomer (about 85 mole %). $^1$H NMR ($C_6D_6$) δ 6.74 (s, 4H, m-H-Mes), 6.08 (s, 2H, =CH), 4.14 (s, 5H, Cp), 2.13 (s, 6H, p-Me-Mes), 1.62 (s, 12H, o-Me-Mes), −1.11 (br s, 2H, WH). $^1$H NMR (THF-$d_8$, −30° C.) δ 7.82 (s, 2H, =CH), 7.17 (s, 4H, m-H-Mes), 5.46 (s, 5H, Cp), 2.37 (s, 6H, p-Me-Mes), 2.06 (s, 12H, o-Me-Mes), −0.7 (br s, $v_{1/2}$=1400 Hz, 2H, WH). $_1$H NMR (THF-$d_8$, −100° C.) δ 7.95 (s, 2H, =CH), 7.19 (s, 4H, m-H-Mes), 5.59 (s, 5H, Cp), 2.38 (s, 6H, p-Me-Mes), 2.07 (s, 12H, o-Me-Mes), 1.19 (br s, $v_{1/2}$=13 Hz, 1H, WH), −2.97 (~br d, $v_{1/2}$=12 Hz, $^1J_{HH}$=3 Hz, $^1J_{HW}$=34 Hz, 1H, WH). $^{13}C\{^1H\}$ NMR (THF-$d_8$, −100° C.) δ 205.2 and 203.1 (s, W-CO), 160.7 (s, NCN), 148.8 (br d, $^1J_{CF}$=242 Hz, o-$C_6F_5$), 141.0 (br s, p-Mes or i-Mes), 139.0 (dm, $^1J_{CF}$=242 Hz, p-$C_6F_5$), 138.5 (s, p-Mes or i-Mes), 137.0 (dm, $^1J_{CF}$=247 Hz, m-$C_6F_5$), 136.4 (br s, o-Mes), 130.6 and 130.5 (s, m-Mes), 127.9 (br s, =CH), 124.5 (br m, i-$C_6F_5$), 88.6 (s, Cp), 21.2 (s, p-Me-Mes), 18.7 and 18.3 (s, o-Me-Mes). $^{19}$F NMR (THF-$d_8$, −30° C.) δ −133.5 (d, 8F, $^3J_{FF}$=11 Hz, o-$C_6F_5$), −164.9 (t, 4F, $^3J_{FF}$=21 Hz, p-$C_6F_5$), −168.5 (t, 8F, $^3J_{FF}$=m-$C_6F_5$). IR (THF-$d_8$)ν(CO)=2063 (vs) and 2007 (vs) $cm^{-1}$.

Minor isomer (about 15 mole %). $^1$H NMR ($C_6D_6$) δ 6.57 (br s, 4H, m-H-Mes), 5.97 (br s, 2H, =CH), 3.96 (br s, 5H, Cp), 1.97 (br s, 6H, p-Me-Mes), 1.44 (br s, 12H, o-Me-Mes), −1.25 (br s, 2H, $WH_2$). $^1$H NMR (THF-$d_8$, −30° C.) δ 7.76 (br s, 2H, =CH), 5.28 (s, 5H, Cp).

EXAMPLE 7

Synthesis of $[CpW(CO)_2(IMes)(Et_2C=O)]^+[B(C_6F_5)_4]^-$

In a glovebox $[CpW(CO)_2(IMes)(CH_3Ph)]^+[B(C_6F_5)_4]^-$ (53 mg, 0.038 mmol) and 3-pentanone (300 μL, 2.83 mmol) were mixed to produce a dark purple solution and placed in an NMR tube equipped with a teflon valve. The volatiles were removed in vacuo, and the purple crystalline material was identified as $[CpW(CO)_2(IMes)(Et_2C=O)]^+[B(C_6F_5)_4]^-$. The identification data for this product was a follows:

$^1$H NMR ($C_6D_6$) δ 6.6 (br s, 4H, m-H-Mes), 6.10 (s, 2H, =CH), 4.49 (s, 5H, Cp), 2.08 (s, 6H, p-Me-Mes), 1.9 (br s, 4H, $CH_3CH_2$), 1.70 (br s, 12H, o-Me-Mes), 0.72 (br s, 6H, $CH_3CH_2$). $^1$H NMR ($Et_2C=O$ and a sealed capillary of $CD_2Cl_2$ for lock, −10° C.) δ 8.60 (s, 2H, =CH), 7.85 and 7.75 (br s, 4H, m-H-Mes), 5.98 (s, 5H, Cp), 2.71 (br s, 12H, o-Me-Mes), resonances of p-Me-Mes and Et presumably obscured by solvent. $^{13}C\{1H\}$ NMR (liquid clathrate, $C_6D_6$) δ 244.4 (s, W-CO), 239 (br s, $Et_2C=O$), 177 (br s, NCN), 149.4 (dm, $^1J_{CF}$=244 Hz, o-$C_6F_5$), 141.1 (s, p-Mes or i-Mes; other resonance presumably obscured by signals around 138), 139.2 (dm, $^1J_{CF}$=246 Hz, p-$C_6F_5$), 137.3 (dm, $^1J_{CF}$=246 Hz, m-$C_6F_5$), 136.1 (bs s, o-Mes), m-Mes and =CH obscured by solvent at 130–127, 125.4 (br m, i-$C_6F_5$), 97 (br s, Cp), 36.6 (br s, $CH_3CH_2$), 20.9 (s, p-Me-Mes), 18.0 (br s, o-Me-Mes), 8 (br s, $CH_3CH_2$). $^{13}C\{^1H\}$ NMR ($Et_2C=O$ and a sealed capillary of $CD_2Cl_2$ for lock, –30° C.) δ 248.1 and 246.4 (s, W-CO), 241.1 (s, $Et_2C=O$), 177.4 (s, NCN), 148.7 (dm, $^1J_{CF}$=244 Hz, o-$C_6F_5$), 140.8 (br s, p-Mes or i-Mes), 138.7 (dm, $^1J_{CF}$=247 Hz, p-$C_6F_5$), 136.9 (s, p-Mes or i-Mes), 136.7 (dm, $^1J_{CF}$=247 Hz, m-$C_6F_5$), 136.7 (s, o-Mes), 130.2 (s, m-Mes), 128 and 126 (br s, =CH), 124.6 (br m, i-$C_6F_6$), 96.0 (s, Cp), 37.8 (s, $CH_3CH_2$), 21.0 (s, p-Me-Mes), 18.8, 18.6, and 17.9 (s, o-Me-Mes), 8.9 (s, $CH_3CH_2$), $^{19}F$ NMR δ ($Et_2C=O$ and a sealed capillary of $CD_2Cl_2$ for lock, –30° C.) –133.3 (dm, 8F, $^3J_{FF}$=11Hz, o-$C_6F_5$), –164.3 (tm, 4F, $^3J_{FF}$=21 Hz, p-$C_6F_5$), –168.2 (tm, 8F, $^3J_{FF}$=17 Hz, m-$C_6F_5$). IR (THF)ν(CO)=1963 (vs) and 1863 (vs), ν($Et_2C=O$)=1718 (w) $cm^{-1}$. UV(toluene)$\lambda_{max}$= 498 nm (ε=1·$10^3$ L·$mol^{-1}cm^{-1}$).

EXAMPLE 8

Synthesis of $[CpW(CO)_2(IMes)(SiEt_3)H]^+$ $[B(C_6F_5)_4]^-$

In a glovebox, a solution of $HSiEt_3$ (16 μL, 0.10 mmol) in 0.5 mL of diethyl ether was added to $[CpW(CO)_2(IMes)(CH_3Ph)]^+[B(C_6F_5)_4]^-$ (69 mg, 0.050 mmol). The sample was stirred for 10 minutes, and the volatiles were removed in vacuo to produce $[CpW(CO)_2(IMes)(SiEt_3)H]^+[B(C_6F_5)_4]^-$ as a brown-yellow product. Two isomers were isolated and their identification data is set forth below.

Major isomer (about 70 mole % at 25° C.): $^1H$ NMR ($C_6D_6$) δ 6.74 and 6.69 (s, 2H, m-H-Mes), 6.12 (s, 2H, =CH), 4.64 (s, 5H, Cp), 2.11 (s, 6H, p-Me-Mes), 1.78 and 1.71 (s, 6H, o-Me-Mes), 0.67 (t, 9H, $^3J_{HH}$=8 Hz, $CH_3CH_2$), 0.31 (dq, 6H, $^3J_{HH}$=2 and 8 Hz, $CH_3CH_2$), –2.60 (s, 1H, $^1J_{HW}$=36 Hz, WH). $^{13}C\{^1H\}$ NMR (liquid clathrate, $C_6D_6$) δ 217.2 (br s, CO), 172.3 (s, $^1J_{HW}$=134 Hz, NCN), 149.5 (br d, $^1J_{CF}$=244 Hz, o-$C_6F_5$), 141.0 (s, p-Mes or i-Mes), 139.3 (dm, $^1J_{CF}$=250 Hz, p-$C_6F_5$), 137.4 (dm, $^1J_{CF}$=250 Hz, m-$C_6F_5$), 136.9 (s, p-Mes or i-Mes), 135.7 (s, o-Mes), 130.4 (br s, m-Mes), 125.5 (br m, i-$C_6F_5$), 125.4 (s, =CH), 92.2 (s, Cp), 21.1 (s, p-Me-Mes), 18.1 (br s, o-Me-Mes), 5.9 (s, $CH_3CH_2$), 4.7 (s, $^1J_{CSi}$=59 Hz, $CH_3CH_2$). $^{19}F$ NMR δ ($C_6D_6$) –133.1 (br, s 8F, o-$C_6F_3$), –164.1 (t, 4F, $^3J_{FF}$=20 Hz, p-$C_6F_5$), –167.9 (br s, 8F, m-$C_6F_5$). $^{29}Si$ NMR δ ($C_6D_6$) 43.2 (s, W-Si). IR (THF-$d_8$)ν(CO)=1979 (vs) and 1948 (vs) $cm^{-1}$.

Minor isomer (about 30 mole % at 25° C.): $^1H$ NMR ($C_6D_6$) δ 6.60 and 6.56 (br s, 2H, m-H-Mes), 6.05 (br s, 2H, =CH), 4.46 (br s, 5H, Cp), 1.99 (br s, 6H, p-Me-Mes), 1.63 and 1.56 (br s, 6H, o-Me-Mes), 0.54 (br t, 9H, $^3J_{HH}$=8 Hz, $CH_3CH_2$), 0.20 (br q, 6H, $^3J_{HH}$=8 Hz, $CH_3CH_2$), –2.69 (s, 1H, $^1J_{HW}$=36 Hz, WH).

EXAMPLE 9

Catalytic Hydrogenation of 3-pentanone

In this example, $CpW(CO)_2(IMes)^+B(C_6F_5)_4^-$ (26.5 mg, 0.019 mmol) as prepared in Example 5 and 3-pentanone (600 μL, 5.65 mmol) were placed in a glass tube. (125 mL capacity) equipped with a teflon valve and the tube was placed in a glove box. The solution was freeze-pump-thawed, frozen again, and the entire tube was submersed in liquid nitrogen. The tube was then filled with about 1.1 atm $H_2$, sealed, and warmed to room temperature. As a result the tube contained 20.1 mmol of $H_2$ at about 4.1 atm and room temperature. The reaction was carried out at 50° C. in a constant-temperature bath. Aliquots were removed by cooling the tube to 77° K., evacuating $H_2$, refilling the tube with Ar, and taking it into the glovebox. After removal of an aliquot of about 60 μL, the tube was again freeze-pump-thawed, then filled with 1.1 atm $H_2$ at 77K and re-sealed. The aliquot was diluted in 500 μL of each $C_6D_6$, and the solution was analyzed by $^1H$ NMR. After 1 hour, TON(total) was 1.0 of which TON(ether) was 0. After 23 hours, TON (total) was 15.1, of which TON(ether) was 0.4. After 6.8 days, TON(total) was 29.9, of which TON(ether) was 0.7, representing a total of 10% conversion of the initial ketone.

EXAMPLE 10

Catalytic Hydrogenation of 3-Pentanone

This example is similar to Example 9 above, except that the reaction was carried out at 23° C. $CpW(CO)_2(IMes)^+B(C_6F_5)_4^-$ (13.3 mg, 0.010 mmol) and 3-pentanone (300 μL, 2.83 mmol) were used according to the same procedure as described for Example 6. After 24 hours, TON(total) was 2.1, of which TON(ether) was 0. After 9.9 days, TON(total) was 10.0, of which TON(ether) was 0, representing a total of 3% conversion of the initial ketone.

EXAMPLE 11

Catalytic Hydrogenation of 3-Pentanone

This example is similar to Example 10, except that it was carried out at high pressure of $H_2$ of about 800 psi. $CpW(CO)_2(IMes)^+B(C_6F_5)_4^-$ (53.0 mg, 0.040 mmol) and 3-pentanone (1.20 mL, 11.3 mmol) were placed in a stainless steel high pressure vessel in a glove box. The vessel was sealed and removed from the glovebox. $H_2$ was added at 800 psi, and the reaction was carried out at room temperature. Prior to removal of each sample for analysis, the bottom of the high pressure vessel was cooled at 77° K., and the pressure was slowly vented. The sample for NMR analysis was taken in a glove box under an argon atmosphere, and the vessel was resealed and repressurized with $H_2$. After 24 hours, TON(total) was 7.8, of which TON(ether) was 0.2. After 10.0 days, TON(total) was 86, of which TON(ether) was 6, representing a total of 29% conversion of the initial ketone.

EXAMPLE 12

Catalytic Hydrogenation of 3-Pentanone

This example is similar to Example 11 (800 psi of $H_2$), except that the reaction was carried out at 50° C. $CpW(CO)_2(IMes)^+B(C_6F_5)_4^-$ (13.3 mg, 0.010 mmol) and 3-pentanone (300 μL, 2.83 mmol) were placed in a stainless steel high pressure vessel in a glove box. $H_2$ was added at 800 psi initial at room temperature, and the reaction as carried out at 50° C. Prior to removal of each sample for analysis, the bottom of the high pressure was cooled at 77° K., and the pressure was slowly vented. After 24 hours, TON(total) was 15.9, of which TON(ether) was 3.8. After 7.0 days, TON (total) was 60.9, of which TON(ether) was 12.6, representing a total of 21% conversion of the initial ketone.

EXAMPLE 13

Catalytic Hydrogenation of 3-Pentanone

This example is similar to Example 9 (50° C.), except that a Mo-based catalyst was used instead of W. $CpMo(CO)_2(IMes)^+B(C_6F_5)_4^-$ (13.3 mg, 0.010 mmol) prepared according to Example 4 and 3-pentanone (300 μL, 2.83 mmol)

were used for the same procedure as described for Example 6. After 24 hours, TON(total) was 0.8, of which TON(ether) was 0. After 9.9 days, TON(total) was 1.0, of which TON(ether) was 0, representing a total of 0.3% conversion of the initial ketone.

EXAMPLE 14

Catalytic Hydrogenation of 3-Pentanone

This example is similar to Example 10 (23° C.), except that Mo-based catalyst was used instead of W. $CpMo(CO)_2(IMes)^+B(C_6F_5)_4^-$ (13.3 mg, 0.010 mmol) prepared according to Example 4 and 3-pentanone (300 µL, 2.83 mmol) were used according to the same procedure as described for Example 7. After 24 hours, TON(total) was 0.9, of which TON(ether) was 0. After 9.9 days, TON(total) was 0.9, of which TON(ether) was 0, representing a total of 0.3% conversion of the initial ketone.

EXAMPLE 15

Catalytic Hydrosilylation of 3-Pentanone

In a glove box $CpW(CO)_2(IMes)^+B(C_6F_5)_4^-$ (4.1 mg, 0.003 mmol), prepared according to Example 5 and 3-pentanone (159 µl, 1.50 mmol), and $HSiEt_3$ (288 µL, 1.80 mmol) were placed in an NMR tube equipped with a teflon valve. Two sealed capillaries with $C_6D_6$ were placed in the same tube for NMR lock purpose. The tube was shaken to mix the ingredients producing a deep purple homogeneous solution. The color faded to light purple within 2 minutes. The reaction was carried out at 23° C. The progress of the reaction was periodically monitored by 1H NMR. At high conversions polarity of the medium drastically decreased. A light purple precipitate was formed and the solution turned colorless. After 15 minutes, TON(alkoxysilane) was 373, TON(ether)=13, and TON(2-pentene) was 16. After 1 hour, TON(alkoxysilane)=466, TON(ether) was 14, and TON(2-pentene) was 21, representing a total of 100% conversion of the initial ketone. The liquid was decanted, and the solid catalyst was re-used without any significant loss of activity or selectivity. The recycled active catalyst was identified by NMR as a mixture of $[CpW(CO)_2(IMes)(SiEt_3)H]^+[B(C_6F_5)_4]^-$ and $[CpW(CO)_2(IMes)(H)_2]^+[B(C_6F_5)_4]^-$.

EXAMPLE 16

Catalytic Hydrosilylation of 3-Acetophenone

This example is similar to Example 15, except that acetophenone was used instead of 3-pentanone. In a glove box, $CpW(CO)_2(IMes)^+B(C_6F_5)_4^-$ (4.1 mg, 0.003 mmol), acetophenone (175 µL, 1.50 mmol), $HSiEt_3$ (288 µL, 1.80 mmol), and two seated capillaries with $C_6D_6$ were placed in an NMR tube equipped with a teflon value. The reaction was carried out at 23° C. The solution remained homogeneous, and the color gradually changed from purple to light yellow. After 15 minutes, TON(alkoxysilane) was 26 and TON(ethylbenzene) was 0. After 23 hours, TON(alkoxysilane) was 446, TON(ethylbenzene) was 11, representing a total of 100% conversion of the initial ketone.

The same procedures as described in Examples 15 and 16 above were used for hydrosilylation of other aromatic ketones. The results are presented in Table 1 below.

TABLE 1

Hydrosilylation of Carbonyl Compounds by W and Mo Catalysts

| # | catalyst[a] (T, °C.) | silane | silane/ substrate ratio | substrate | products | initial TOF[b] h$^{-1}$ | total TON[c] (yield, %) | time hours |
|---|---|---|---|---|---|---|---|---|
| 1 | W (23) | $HSiEt_3$ | 1.2 | (3-pentanone) | $OSiEt_3$ ether | 1490 | 466 (93.2) | 1 |
|   |   |   |   |   | (2-pentene) | 62 | 21 (4.1) |   |
|   |   |   |   |   | (ether product) | 52 | 14 (2.7) |   |
| 2 | Mo (23) | $HSiEt_3$ | 1.2 | (3-pentanone) | $OSiEt_3$ | 10 | 29 (5.8) | 25 |
|   |   |   |   |   | (2-pentene) | n.d.[d] | 1 (0.2) |   |
|   |   |   |   |   | (ether product) | 0 | 0 (0) |   |

TABLE 1-continued

Hydrosilylation of Carbonyl Compounds by W and Mo Catalysts

| # | catalyst[a] (T, °C.) | silane | silane/ substrate ratio | substrate | products | initial TOF[b] h$^{-1}$ | total TON[c] (yield, %) | time hours |
|---|---|---|---|---|---|---|---|---|
| 3 | Mo (53) | HSiEt$_3$ | 1.2 | pentan-3-one | 3-(triethylsilyloxy)pentane | 10 | 12 (2.3) | 1.2 |
|   |   |   |   |   | pent-2-ene | n.d. | 1 (0.2) |   |
|   |   |   |   |   | di(pentan-3-yl) ether | 0 | 0 (0) |   |
| 4 | W (23) | HSiEt$_3$ | 1.2 | acetophenone | 1-phenyl-1-(triethylsilyloxy)ethane | 104 | 446 (89.1) | 23 |
|   |   |   |   |   | ethylbenzene | n.d. | 11 (2.1) |   |
| 5 | Mo (23) | HSiEt$_3$ | 1.2 | acetophenone | 1-phenyl-1-(triethylsilyloxy)ethane | 1 | 12 (2.4) | 23 |
|   |   |   |   |   | ethylbenzene | 0 | 0 (0) |   |
| 6 | Mo (53) | HSiEt$_3$ | 1.2 | acetophenone | 1-phenyl-1-(triethylsilyloxy)ethane | 11 | 111 (22.1) | 23 |
|   |   |   |   |   | ethylbenzene | 0 | 0 (0) |   |
| 7 | W (23) | HSiEt$_3$ | 1.2 | 4'-fluoroacetophenone | 1-(4-fluorophenyl)-1-(triethylsilyloxy)ethane | 66 | 494 (98.7) | 21 |
|   |   |   |   |   | 4-fluoroethylbenzene | 0 | 2 (0.4) |   |
| 8 | W (23) | HSiEt$_3$ | 2.3 | ethyl acetate | EtOSiEt$_3$ | 173 | 468 (93.6) | 26 |
|   |   |   |   |   | Et$_2$O | n.d. | 30 (5.9) |   |

[a]W = CpW(CO)$_2$(IMes)$^+$B(C$_6$F$_5$)$_4^-$, Mo = CpMo(CO)$_2$(IMes)$^+$B(C$_6$F$_5$)$_4^-$
[b]initial TOF is an average turnover frequency for a given product, measured within the first 15–20 minutes of the reaction.
[c]total TON is a total number of turnovers for a given product, measured at the end of the reaction. The end of the reaction is defined either by complete conversion of the substrate (organic carbonyl compound) or by complete decomposition of the catalysts to unreactive species.
[d]n. d.—not determined

EXAMPLE 17

Catalytic Hydrosilylation of an Ester

This example is similar to Example 15, except that hydrosilylation of an ester required 2 equivalents of $HSiEt_3$ per 1 equivalent of substrate. In a glove box, $CpW(CO)_2(IMes)^+B(C_6F_5)_4^-$ (2.8 mg, 0.002 mmol), ethyl acetate (98 µL, 1.00 mmol), $HSiEt_3$ (352 µL, 2.20 mmol), and two sealed capillaries with $C_6D_6$ were placed in an NMR tube equipped with a teflon valve. The reaction was carried out at 23° C. At high conversions the polarity of the medium drastically decreased. A light purple precipitate was formed and solution turned colorless. After 18 minutes, TON (alkoxysilane) was 52 and TON(ether) was 0. After 26 hours, TON(alkoxysilane) was 468 and TON(ether) was 30, representing a total of 100% conversion of the initial ester.

EXAMPLE 18

Catalytic Hydrosilylation of an Aldehyde

This example is similar to Example 15, except that 1-heptanal was used instead of 3-pentanone. In a glove box $CpW(CO)_2(IMes)^+B(C_6F_5)_4^-$ (4.1 mg, 0.003 mmol), 1-heptanal (209 µL, 1.50 mmol), $HSiEt_3$ (288 µL, 1.80 mmol), and two sealed capillaries with $C_6D_6$ were placed in an NMR tube equipped with a teflon valve. The reaction was carried out at 23° C. At high conversions polarity of the media drastically decreased. A light yellow precipitate was formed and solution turned light yellow. After 15 minutes, TON(alkoxysilane) was 248 and TON(ether) was 96. After 1.5 hours, TON(alkoxysilane)=295 and TON(ether)=105, representing a total of 81% yield and a 100% consumption of the initial aldehyde.

What is claimed is:

1. A compound is provided including an organometallic complex represented by the formula I:

wherein M is an atom of molybdenum or tangsten, Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radical, $C_{1-20}$ hydrocarbyl radical, substituted hydrocarbyl radical, halogen radical, halogen-substituted hydrocarbyl radical, —OR, —C(O)R', —CO₂R', —SiR'₃ and —NR'R", wherein R' and R" are independently selected from the group consisting of H radical, $C_{1-20}$ hydrocarbyl radical, halogen radical, and halogen-substituted hydrocarbyl radical, wherein said $Q^1$ to $Q^5$ radicals are optionally linked to each other to form a stable bridging group, NHC is any N-heterocyclic carbene ligand, L is either any neutral electron donor ligand, wherein k is a number from 0 to 1 or L is an anionic ligand wherein k is 2, and A⁻ is an anion.

2. The compound according to claim 1, wherein NHC is an unsubstituted or substituted N-heterocyclic carbene selected from the group consisting of carbenes represented by formula III

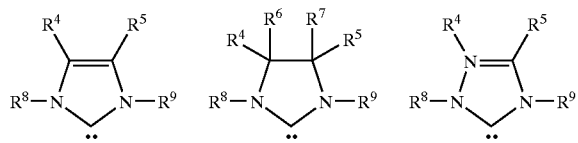

wherein $R^4$, $R^5$, $R^6$, $R^7$, $R^8$ and $R^9$ are each independently hydrogen, halogen or a substituent selected from the group consisting of $C_1-C_{20}$ alkyl, $C_2-C_{20}$ alkenyl, $C_2-C_{20}$ alkynyl, aryl, $C_1-C_{20}$ carboxylate, $C_1-C_{20}$ alkoxy, $C_2-C_{20}$ alkenyloxy, $C_2-C_{20}$ alkynyloxy, aryloxy, $C_2-C_{20}$ alkoxycarbonyl, $C_1-C_{20}$ alkylthiol, aryl thiol, $C_1-C_{20}$ alkylsulfonyl and $C_1-C_{20}$ alkylsulfinyl, wherein further each $R^4$, $R^5$, $R^6$, $R^7$, $R^8$ and $R^9$ is optionally substituted with one or more moieties selected from the group consisting of $C_1-C_{20}$ hydrocarbyl, $C_1-C_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen, wherein $R^4$, $R^5$, $R^6$, $R^7$, $R^8$ and $R^9$ radicals are optionally linked to each other to form a stable bridging group.

3. The compound according to claim 1, wherein L is selected from the group consisting of a hydrocarbon or halogenated hydrocarbon solvent molecule, a dihydrogen ($H_2$) or hydrosilane, a ketone, an aldehyde or an ester substrate, an alkoxysilane, ether or alcohol product molecule, a combination of two anionic ligands selected from the group consisting of hydride (H⁻), silyl $(SiR^{10}R^{11}R^{12})^-$ and mixtures thereof, wherein $R^{10}$, $R^{11}$, $R^{12}$ are independently hydrogen, halogen or a substituent selected from the group consisting of $C_1-C_{20}$ alkyl, $C_2-C_{20}$ alkenyl, $C_2-C_{20}$ alkynyl, aryl, $C_1-C_{20}$ carboxylate, $C_1-C_{20}$ alkoxy, $C_2-C_{20}$ alkenyloxy, $C_2-C_{20}$ alkynyloxy, aryloxy, $C_2-C_{20}$ alkoxycarbonyl, $C_1-C_{20}$ alkylthiol, aryl thiol, $C_1-C_{20}$ alkylsulfonyl and $C_1-C_{20}$ alkylsulfinyl, wherein further each $R_{10}$, $R_{11}$, $R^{12}$ is optionally substituted with one or more moieties selected from the group consisting of $C_1-C_{20}$ hydrocarbyl, $C_1-C_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen.

4. The compound according to claim 1, wherein said anion (A⁻) is selected from the group consisting of $BF_4^-$, $PF_6^-$, $SbF_6^-$, $CF_3SO_3^-$, $CB_{11}H_{12}^-$, $CB_9H_{10}^-CB_9H_5X_5^-$, $CB_{11}H_6X_6^-$, wherein X is F Cl, Br or I, $HBR_3^-$, wherein R is a hydrocarbyl or substituted hydrocarbyl, and $[(M')Z^1Z^2...Z^n]^-$, M' is an element selected form atoms of group 13, n is the total number of Z ligands or n is 4, and $Z^1$ to $Z^n$ are independently selected from the group consisting of H radical, $C_{1-20}$ hydrocarbyl radical, substituted hydrocarbyl radical, halogens, halogen-substituted hydrocarbyl radical, hydrocarbyl-, halogen-substituted hydrocarbyl organometalloid radical, —OR, —C(O)R', —CO₂R', and —NR'R", wherein R' and R" are independently selected from the group consisting of H radicals, $C_{1-20}$ hydrocarbyl radicals, halogens, and halogen-substituted hydrocarbyl radical; said $Z^1$ to $Z^n$ radicals optionally linked to each other to form a stable bridging group.

5. The compound according to claim 4, wherein M' is boron.

6. The compound according to claim 4, wherein said $Z^1$ to $Z^n$ are each fluorine substituted phenyl, naphthyl or anthracenyl radical.

7. The compound according to claim 1, further comprising a solvent of crystallization thereby forming $[CpW(CO)_2(NHC)L_k]^+[A]^-.Y'_h$, wherein h is a number from 0 to 1 and Y' is selected from the group consisting of a $C_{1-20}$ hydrocarbon, an aromatic hydrocarbon, a $C_{1-20}$ halocarbon, an ether and mixtures thereof.

8. The compound according to claim 7, wherein Y' is selected from the group consisting of hexane, benzene, toluene, tetrahydrofuran, diethyl ether and mixtures thereof.

9. A method of preparing a catalytic composition comprising an organometallic complex represented by formula I:

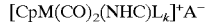

wherein M is a molybdenum or tungsten, Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radical, $C_{1-20}$ hydrocarbyl radical, substituted hydrocarbyl radical, halogen radical, halogen-substituted hydrocarbyl radical, —OR, —C(O)R', —CO$_2$R', —SiR'$_3$, and —NR'R", wherein R' and R" are independently selected from the group consisting of H radical, $C_{1-20}$ hydrocarbyl radical, halogen radical, and halogen-substituted hydrocarbyl radical, wherein said $Q^1$ to $Q^5$ radicals are optionally linked to each other to form a stable bridging group, NHC is any N-heterocyclic carbene ligand, L is either any neutral ligand, wherein k is a number from 0 to 1 or L is an anionic ligand wherein k is 2, and A is an anion, wherein said catalyst is prepared by reacting a metal hydride represented by the formula II:

$$\text{CpM(CO)}_2\text{(NHC)H} \qquad \text{II}$$

with a hydride removing agent selected from BR$_3$ or a compound represented by formula $Y^+A^-$, wherein Y is selected from the group consisting of (aryl)$_3$C$^+$, (aryl)$_2$HC$^+$, $C_7H_7^+$, $R_3$NH$^+$, Ag$^+$ and $(C_5R_5)_2$Fe$^+$, wherein R is a hydrocarbyl or substituted hydrocarbyl, A$^-$ is an anion selected from the group consisting of BF$_4^-$, PF$_6^-$, SbF$_6^-$, CF$_3$SO$_3^-$, CB$_{11}$H$_{12}^-$, CB$_9$H$_{10}^-$, CB$_9$H$_5$X$_5^-$, CB$_{11}$H$_6$X$_6^-$, wherein X is F Cl, Br or I, HRB$_3$—, wherein R is a hydrocarbyl or substituted hydrocarbyl and $[(M')Z^1 Z^2 \ldots Z^n]^-$, M' is an element selected from atoms of group 13, n is the total number of Z ligands or n is 4, and $Z^1$ to $Z^n$ are independently selected from the group consisting of H radical, $C_{1-20}$ hydrocarbyl radical, substituted hydrocarbyl radical, halogens, halogen-substituted hydrocarbyl radical, hydrocarbyl-, halogen-substituted hydrocarbyl organometalloid radical, —OR, —C(O)R', —CO$_2$R', and —NR'R", wherein R' and R" are independently selected from the group consisting of H radicals, $C_{1-20}$ hydrocarbyl radical, halogens, and halogen-substituted hydrocarbyl radical; said $Z^1$ to $Z^n$ radicals optionally linked to each other to form a stable bridging group.

10. The method according to claim 9, wherein said metal hydride is prepared by reacting a phosphine hydride represented by the formula V $$\text{CpM(CO)}_2\text{(PR}_3\text{)H} \qquad \text{V}$$

wherein R is any $C_1$–$C_{20}$ hydrocarbyl group with said NHC.

11. The method according to claim 9, wherein NHC is an unsubstituted or substituted N-heterocyclic carbene selected from the group consisting of

III

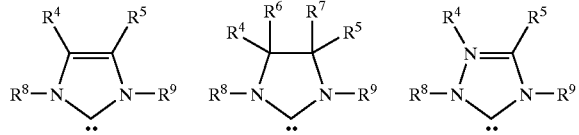

wherein $R^4$, $R^5$, $R^6$, $R^7$, $R^8$ and $R^9$ are each independently hydrogen, halogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein further each $R^4$, $R^5$, $R^6$, $R^7$, $R^8$ and $R^9$ is optionally substituted with one or more moieties selected from the group consisting of $C_1$–$C_{20}$ hydrocarbyl, $C_1$–$C_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen, wherein said $R^4$, $R^3$, $R^6$, $R^7$, $R^8$ and $R^9$ radicals are optionally linked to each other to form a stable bridging group.

12. The method according to claim 9, wherein said L is a hydrocarbon or halogenated hydrocarbon solvent molecule, a dihydrogen (H$_2$) or hydrosilane, a ketone, an aldehyde or an ester substrate, an alkoxysilane, ether or alcohol product molecule, a combination of two anionic ligands selected from the group consisting of hydride (H$^-$), silyl (SIR$^{10}$R$^{11}$R$^{12}$)$^-$ and mixtures thereof, wherein R$^{10}$, R$^{11}$, R$^{12}$ are independently hydrogen, halogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, wherein further each R$^{10}$, R$^{11}$, R$^{12}$ is optionally substituted with one or more moieties selected from the group consisting of $C_1$–$C_{20}$ hydrocarbyl, $C_1$–$C_{20}$ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen.

13. A process for the catalytic hydrogenation of an organic compound which contains at least one reducible functional group selected from the group consisting of R(C=O)R$^1$ and R(C=O)H, wherein R and R$^1$ are each independently selected from hydrogen (H) or any $C_1$–$C_{30}$ hydrocarbyl radicals and substituted hydrocarbyl radicals, which can be the same or different, said process comprising contacting said organic compound with hydrogen in the presence of a catalyst to form a reaction mixture, wherein said catalyst comprises an organometallic complex represented by the formula I:

$$[\text{CpM(CO)}_2\text{NHC)L}_k]^+\text{A}^- \qquad \text{I}$$

wherein M is a molybdenum or tungsten atom Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radical, $C_{1-20}$ hydrocarbyl radical, substituted hydrocarbyl radical, halogen radical, halogen-substituted hydrocarbyl radical, —OR, —C(O)R'—CO$_2$R', —SiR'$_3$ and —NR'R", wherein R' and R" are independently selected from the group consisting of H radical, $C_{1-20}$ hydrocarbyl radical, halogen radical, and halogen-substituted hydrocarbyl radical, wherein said $Q^1$ to $Q^5$ radicals are optionally linked to each other to form a stable bridging group, NHC is any N-heterocyclic carbene ligand, L is either any neutral electron donor ligand, wherein k is a number from 0 to 1 or L is an anionic ligand wherein k is 2, and A$^-$ is an anion.

14. The process according to claim 13, wherein NHC is an unsubstituted or substituted N-heterocyclic carbene selected from the group consisting of

III

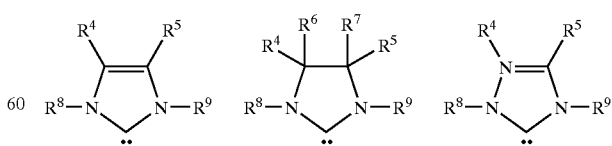

wherein $R^4$, $R^5$, $R^6$, $R^7$, $R^8$ and $R^9$ are each independently hydrogen, halogen or a substituent selected from the group consisting of $C_1$–$C_{20}$ alkyl, $C_2$–$C_{20}$ alkenyl, $C_2$–C20 alkynyl, aryl, $C_1$–$C_{20}$ carboxylate, $C_1$–$C_{20}$ alkoxy, $C_2$–$C_{20}$ alkenyloxy, C₂–C₂₀ alkynyloxy, aryloxy, C₂–C₂₀ alkoxycarbonyl, C₁–C₂₀ alkylthiol, aryl thiol, C₁–C₂₀ alkylsulfonyl and C₁–C₂₀ alkylsulfinyl, wherein further each $R^4$, $R^5$, $R^6$, $R^7$, $R^8$ and $R^9$ is optionally substituted with one or more moieties selected from the group consisting of C₁–C₂₀ hydrocarbyl, C₁–C₂₀ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen, wherein said $R^4$, $R^5$, $R^6$, $R^7$, $R^8$ and $R^9$ radicals are optionally linked to each other to form a stable bridging group.

15. The process according to claim 13, wherein L is selected from the group consisting of a hydrocarbon or halogenated hydrogen solvent molecule, a dihydrogen ($H_2$) or dihydride ($H^-$)₂, a ketone, an aldehyde, ether or alcohol product molecule, and mixtures thereof.

16. The process according to claim 13, wherein said anion ($A^-$) is selected from the group consisting of $A^-$ is an anion selected from the group consisting of $BF_4^-$, $PF_6^-$, $SBF_6^-$, $CF_3SO_3^-$, $CB_{11}H_{12}^-$, $CB_9H_{10}^-$, $CB_9H_5X_5^-$, $CB_{11}H_6X_6^-$, wherein X is F Cl, Br or I, $HBR_3^-$, wherein R is a hydrocarbyl or substituted hydrocarbyl, and $[(M')Z^1 Z^2 \ldots Z^n]^-$, M' is an element selected from atoms of group 13, n is the total number of Z ligands or n is 4, and $Z^1$ to $Z^n$ are independently selected from the group consisting of H radical, C₁₋₂₀ hydrocarbyl radical, substituted hydrocarbyl radical, halogens, halogen-substituted hydrocarbyl radical, hydrocarbyl-, halogen-substituted hydrocarbyl organometalloid radical, —OR, —C(O)R', —CO₂R', and —NR'R", wherein R' and R" are independently selected from the group consisting of H radicals, C₁₋₂₀ hydrocarbyl radical, halogens, and halogen-substituted hydrocarbyl radical; said $Z^1$ to $Z^n$ radicals optionally linked to each other to form a stable bridging group.

17. The process according to claim 16, wherein M' is boron.

18. The process according to claim 16, wherein said $Z^1$ to $Z^n$ are each fluorine substituted phenyl, naphthyl or anthracenyl radicals.

19. The process according to claim 15, wherein said solvent molecule is any C₁₋₂₀ hydrocarbon, aromatic hydrocarbon, C₁₋₂₀ halocarbon, ether, or the organic compound subjected to hydrogenation and mixtures thereof.

20. The process according to claim, 13, wherein said catalyst further comprises a solvent of crystallization thereby forming $[CpW(CO)_2(NHC)L_k]^+[A]^-·Y_h$, wherein h is a aromatic hydrocarbon, C₁₋₂₀ hydrocarbon, on ether and mixtures thereof.

21. The process according to claim 13, wherein said process is carried out at a pressure of from about 1 atmosphere to about 5000 psi and at a temperature of from about 95° C. about 100° C.

22. The process according to claim 13, wherein said process is carried out at a pressure of from about 1 atmosphere to about 800 psi and at a temperature of from about 20° C. about 100° C.

23. A process for the catalytic hydrosilylation of an organic compound which contains at least one functional group selected from the group consisting of R(C=O)R¹ and R(C=O)H, and R(CO₂)R¹, wherein R and R¹ are each independently selected from hydrogen, C₁₋₃₀ hydrocarbyl radicals or substituted hydrocarbyl radicals, said process comprising contacting said organic compound in the presence of hydrosilane with a catalyst to form a mixture, said catalyst comprising an organometallic complex represented by the formula I:

$[CpM(CO)_2NHC)L_k]^+A^-$  I wherein M is a molybdenum or tungsten atom Cp is substituted or unsubstituted cyclopentadienyl radical represented by the formula $[C_5Q^1Q^2Q^3Q^4Q^5]$, wherein $Q^1$ to $Q^5$ are independently selected from the group consisting of H radical, C₁₋₂₀ hydrocarbyl radical, substituted hydrocarbyl radical, halogen radical, halogen-substituted hydrocarbyl radical, —OR, —C(O)R'—CO₂R', —SiR'₃ and —NR'R", wherein R' and R" are independently selected from the group consisting of H radical, C₁₋₂₀ hydrocarbyl radical, halogen radical, and halogen-substituted hydrocarbyl radical, wherein said $Q^1$ to $Q^5$ radicals are optionally linked to each other to form a stable bridging group, NHC is any N-heterocyclic carbene ligand, L is either any neutral electron donor ligand, wherein k is a number from 0 to 1 or L is an anionic ligand wherein k is 2, and $A^-$ is an anion.

24. The process according to claim 23, wherein NHC is an unsubstituted or substituted N-heterocyclic carbene selected from the group consisting of

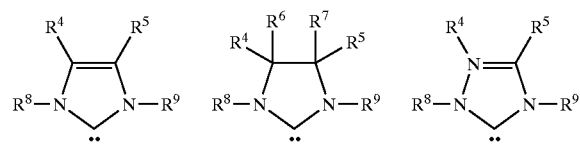

III wherein $R^4$, $R^5$, $R^6$, $R^7$, $R^8$ and $R^9$ are each independently hydrogen, halogen or a substituent selected from the group consisting of C₁–C₂₀ alkyl, C₂–C₂₀ alkenyl, C₂–C20 alkynyl, aryl, C₁–C₂₀ carboxylate, C₁–C₂₀ alkoxy, C₂–C₂₀ alkenyloxy, C₂–C₂₀ alkynyloxy, aryloxy, C₂–C₂₀ alkoxycarbonyl, C₁–C₂₀ alkylthiol, aryl thiol, C₁–C₂₀ alkylsulfonyl and C₁–C₂₀ alkylsulfinyl, wherein further each $R^4$, $R^5$, $R^6$, $R^7$, $R^8$ and $R^9$ is optionally substituted with one or more moieties selected from the group consisting of C₁–C₂₀ hydrocarbyl, C₁–C₂₀ alkoxy, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen, wherein said $R^4$, $R^5$, $R^6$, $R^7$, $R^8$ and $R^9$ radicals are optionally linked to each other to form a stable bridging group.

25. The process according to claim 23, wherein L is selected from the group consisting of a hydrocarbon or halogenated hydrocarbon solvent melocule, a dihydrogen ($H_2$) or hydrosilane, a ketone, an aldehyde or an ester substrate, an alkoxysilane, ether or alcohol product molecule, a combination of two anionic ligands selected from the group consisting of hydride ($H^-$), silyl $(SiR^{10}R^{11}R^{12})^-$ and mixtures thereof, wherein $R^{10}$, $R^{11}$, $R^{12}$ are independently hydrogen, halogen or a substituent selected form the group consisting of C₁–C₂₀ alkyl, C₂–C₂₀ alkenyl, C₂–C₂₀ alkynyl, aryl, C₁–C₂₀ alkoxy, C₂–C₂₀ alkenyloxy, C₂–C₂₀ alkynyloxy, aryloxy, C₂–C₂₀ alkoxycarbonyl, C₁–C₂₀ alkylthiol, aryl thiol, C₁–C₂₀ alkylsulfonyl and C₁–C₂₀ alkylsulfinyl, wherein further each $R^{10}$, $R^{11}$, $R^{12}$ is optionally substituted with one or more moieties selected from the group consisting of C₁–C₂₀ hydrocarbyl, C₁–C₂₀ alkoxy, hydroxyl, thiol, thioether, ketone, aldehyde, ester ether, amine, iminie, amide, nitro, carboxylic acid, disulfide, carbonate, isocyanate, carbodiimide, carboalkoxy, carbamate and halogen.

26. The process according to claim 23, wherein said anion ($A^-$) is selected from the group consisting of is selected from the group consisting of $BF_4^-$, $PF_6^-$, $SbF_6^-$, $CF_3SO_3^-$, $CB_{11}H_{12}^-$, $CB_9H_{10}^-$, $CB_9H_5X_5^-$, $CB_{11}H_6X_6^-$, wherein X is F Cl, Br or I, $HBR_3^-$, wherein R is a hydrocarbyl or substituted hydrocarbyl, and $[(M')Z^1 Z^2 \ldots Z^n]^-$, M' is an element selected from atoms of group 13, n is the total number of Z ligands or n is 4, and $Z^1$ to $Z^n$ are independently selected from the group consisting of H radical, $C_{1-20}$ hydrocarbyl radical, substituted hydrocarbyl radical, halogens, halogen-substituted hydrocarbyl radical, hydrocarbyl-, halogen substituted hydrocarbyl organometalloid radical, —OR, —C(O)R', —CO$_2$R', and —NR'R", wherein R' and R" are independently selected from the group consisting of H radicals, $C_{1-20}$ hydrocarbyl radicals, halogens, and halogen-substituted hydrocarbyl radical; said $Z^1$ to $Z^n$ radical optionally linked to each other to form a stable bridging group.

27. The process according to claim 26, wherein M' is boron.

28. The process according to claim 26, wherein said $Z^1$ to $Z^n$ are each fluorine substituted phenyl, naphthyl or anthracenyl radicals.

29. The according to claim 25, wherein said solvent molecule is any $C_{1-20}$ hydrocarbon, aromatic hydrocarbon, $C_{1-20}$ halocarbon, ether or the organic compound subjected to hydrosilylation and mixtures thereof.

30. The process according to claim 23, wherein said catalyst further comprises a solvent of crystallization thereby forming $[CpW(CO)_2(NHC)L_k]^+[A]^-.Y'_h$, wherein h is a number of 0 to 1 and Y' is selected from the group consisting of a $C_{1-20}$ hydrocarbon and aromatic hydrocarbon, $C_{1-20}$ hydrocarbon, on ether and mixtures thereof.

31. The process according to claim 23, wherein said process is carried out at a temperature of from about −95° C. to about 120° C.

32. The process according to claim 23, wherein said process is carried out at a temperature of from about 200° C. to about 100° C.

\* \* \* \* \*